(12) United States Patent
Leigh

(10) Patent No.: US 8,644,935 B2
(45) Date of Patent: Feb. 4, 2014

(54) METHODS OF FORMING SEALED DEVICES CONTAINING HEAT SENSITIVE COMPONENTS

(75) Inventor: C. Roger Leigh, North Epping (AU)

(73) Assignee: Cochlear Limited, Macquarie University, NSW (AU)

( * ) Notice: Subject to any disclaimer, the term of this patent is extended or adjusted under 35 U.S.C. 154(b) by 692 days.

(21) Appl. No.: 12/597,381

(22) PCT Filed: Apr. 23, 2008

(86) PCT No.: PCT/AU2008/000579
§ 371 (c)(1),
(2), (4) Date: Jan. 14, 2011

(87) PCT Pub. No.: WO2008/131484
PCT Pub. Date: Nov. 6, 2008

(65) Prior Publication Data
US 2011/0106188 A1      May 5, 2011

(30) Foreign Application Priority Data

Apr. 23, 2007 (AU) .................................. 2007902123

(51) Int. Cl.
*A61N 1/372* (2006.01)
(52) U.S. Cl.
USPC ................. 607/36; 607/2; 174/50.5; 206/438
(58) Field of Classification Search
None
See application file for complete search history.

(56) References Cited

U.S. PATENT DOCUMENTS

| 2,495,476 | A | | 1/1950 | Posen |
| 3,798,390 | A | | 3/1974 | Gage |
| 4,010,759 | A | * | 3/1977 | Boer ............................... 607/36 |
| 4,050,956 | A | | 9/1977 | De Bruin |
| 4,419,995 | A | | 12/1983 | Hochmair et al. |
| 4,517,738 | A | | 5/1985 | Fukuoka et al. |
| 4,693,409 | A | | 9/1987 | Mizunoya et al. |
| 4,991,582 | A | | 2/1991 | Byers et al. |
| 5,046,242 | A | | 9/1991 | Kuzma |
| 5,103,818 | A | | 4/1992 | Maston et al. |
| 5,271,397 | A | | 12/1993 | Seligman et al. |
| 5,279,292 | A | | 1/1994 | Raumann et al. |
| 5,411,467 | A | | 5/1995 | Hortmann et al. |

(Continued)

FOREIGN PATENT DOCUMENTS

DE       26 22 245       12/1977
DE       35 36 111       5/1986

(Continued)

OTHER PUBLICATIONS

PowerBook G4 15-inch Users Guide, Apple Computer, Inc., 2005, pp. 1-112.*

(Continued)

*Primary Examiner* — Kennedy Schaetzle
(74) *Attorney, Agent, or Firm* — Kilpatrick, Townsend & Stockton, LLP.

(57) ABSTRACT

An implantable device is provided. The device is constructed from an open body containing electronic components, a heat-sensitive component, and a sealing component. The device is formed in a moisture controlled environment, such that the heat-sensitive component is attached to the open enclosure after the enclosure has been heated. The sealing component is subsequently affixed to the open enclosure to form a sealed enclosure.

11 Claims, 1 Drawing Sheet

(56) References Cited

U.S. PATENT DOCUMENTS

| | | | |
|---|---|---|---|
| 5,620,242 A * | 4/1997 | Leon et al. | 312/223.1 |
| 5,645,586 A | 7/1997 | Meltzer | |
| 5,724,431 A | 3/1998 | Reiter et al. | |
| 5,792,208 A | 8/1998 | Gray | |
| 5,814,091 A * | 9/1998 | Dahlberg et al. | 607/36 |
| 5,814,095 A | 9/1998 | Muller et al. | |
| 5,817,130 A | 10/1998 | Cox et al. | |
| 5,837,558 A | 11/1998 | Zuniga et al. | |
| 5,895,414 A | 4/1999 | Sanchez-Zambrano | |
| 5,984,859 A | 11/1999 | Lesinski | |
| 6,001,129 A | 12/1999 | Bushek et al. | |
| 6,011,993 A | 1/2000 | Tziviskos et al. | |
| 6,038,473 A | 3/2000 | Olson et al. | |
| 6,040,082 A | 3/2000 | Haas et al. | |
| 6,054,682 A | 4/2000 | Ochoa et al. | |
| 6,084,296 A * | 7/2000 | Colello et al. | 257/698 |
| 6,685,452 B2 * | 2/2004 | Christiansen et al. | 417/572 |
| 7,376,465 B2 * | 5/2008 | Hornfeldt et al. | 607/36 |
| 7,729,769 B1 * | 6/2010 | Xie et al. | 607/36 |
| 8,025,236 B2 * | 9/2011 | Mangaroo et al. | 235/472.01 |
| 2005/0088811 A1 * | 4/2005 | Ulla et al. | 361/683 |
| 2007/0213780 A1 | 9/2007 | Rebentisch et al. | |
| 2008/0033500 A1 * | 2/2008 | Strother et al. | 607/36 |
| 2008/0241649 A1 * | 10/2008 | Kohri et al. | 429/96 |
| 2009/0312835 A1 * | 12/2009 | Stevenson | 623/3.1 |
| 2010/0220441 A1 * | 9/2010 | Berlekamp | 361/679.54 |
| 2011/0227536 A1 * | 9/2011 | Bourilkov et al. | 320/112 |

FOREIGN PATENT DOCUMENTS

| | | |
|---|---|---|
| DE | 39 18 329 | 12/1990 |
| DE | 39 40 632 | 12/1990 |
| GB | 1426873 | 3/1976 |
| GB | 2061155 | 5/1981 |
| WO | WO 92/20402 | 11/1992 |
| WO | WO 97/44987 | 11/1997 |
| WO | 2006081361 A2 | 8/2006 |

OTHER PUBLICATIONS

International Search Report. PCT/AU2008/000570. Mailed May 16, 2008.

* cited by examiner

METHODS OF FORMING SEALED DEVICES CONTAINING HEAT SENSITIVE COMPONENTS

CROSS REFERENCE TO RELATED APPLICATIONS

This application is a National Stage of PCT/AU2008/000570, filed Apr. 23, 2008, entitled "IMPLANT ASSEMBLY", which claims priority from Australian Provisional Patent Application No. 2007902123 entitled "IMPLANT ASSEMBLY," filed Apr. 23, 2007. The contents of these applications are hereby incorporated by reference herein.

BACKGROUND

1. Field of the Invention

The present invention relates generally to implantable devices, and particularly to the construction and assembly of such devices.

2. Related Art

The present invention relates to devices intended to be implanted in the human body, particularly those having internal batteries, or other temperature-sensitive components.

For example, active medical devices typically require a source of electrical power. This may be achieved by passing power transcutaneously via an inductive link, or by providing an implanted power source such as an internal battery. Battery power has the advantage of reducing the need for external components, and also avoids the power losses associated with an RF link. Also, batteries which are rechargeable via an inductive link may provide a degree of independent operation.

A number of precautions are necessary to ensure the highest level of reliability of the electronics in an active medical device. One such precaution is ensuring the electronics are enclosed in a hermetically sealed enclosure with a very low moisture level, typically less than 0.5%. To achieve this low moisture level it is necessary to bake the assembly before final sealing of the enclosure. A typical bake would be 125° C. under vacuum for 16 hours. The final seal is typically achieved by sealing a "bake out hole," which is a hole in the enclosure, of about 0.15 mm diameter left open to allow the escape of moisture, and which can be sealed by a laser pulse.

While most electrical components can withstand the bake process, batteries often cannot withstand such temperatures. For example, lithium ion battery technology typically has an upper temperature limit of 60° C. When exposed to temperatures, such a battery is irreversibly damaged. Other temperature-sensitive components in implants may similarly be unable to withstand such bake temperatures.

SUMMARY

In one aspect of the present invention, an implantable device constructed from an open body cochlear implant system is provided. The implantable device contains electronic components, a heat sensitive component, and a sealing component, the device being formed in a moisture controlled environment, such that the heat sensitive component is attached to the open body after the open body has been baked, and the sealing component is affixed to seal the enclosure.

In a second aspect of the present invention, a method of forming an implantable device is provided. The method comprises, baking an open body containing electronic components so as to reduce the moisture content; connecting a heat sensitive component to said open body; and sealing the open body to form said device.

In a third aspect of the present invention, a method of forming a sealed device is provided. The method comprises a sealed device, the device including electronic components and at least one heat sensitive component, the method comprising: baking an open body containing electronic components so as to reduce the moisture content; connecting a heat sensitive component to said open body; and sealing the open body to form said device.

BRIEF DESCRIPTION OF THE DRAWINGS

Illustrative embodiments of the present invention are described herein with reference to the accompanying figures, in which.

DETAILED DESCRIPTION

Embodiments of the present invention will now be described in detail. It will be appreciated that the embodiments are intended to be illustrative and not limiting. In particular, although the exemplary embodiments described herein are presented in the context of cochlear implants and batteries, embodiments of the present invention may be utilized in any implantable device having an enclosure housing heat-sensitive components.

Figure 1:
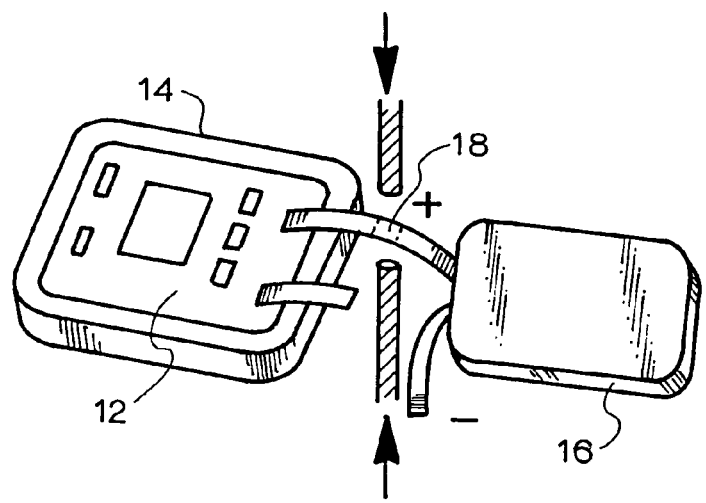
FIG. 1 is a perspective view illustrating one implementation of the present invention.

FIG. 1 shows a construction where electronics 12 are positioned in an implant enclosure 14. Enclosure 14 is open on one side; that is, one side of enclosure 14 has an aperture that, in this illustrative embodiment, is the entire side. To reduce the moisture level in enclosure 14, the enclosure 14 and electronics 12 may be heated such as by baking. In one embodiment, the package of enclosure 14 and electronics 12 is baked in the conventional way, for example at 125° C. under vacuum for 16 hours. One suitable approach is to bake electronics 12 in a vacuum oven attached to a glovebox (not shown) capable of controlling moisture content. Commercial gloveboxes capable of controlling moisture and oxygen levels to as low as a few ppm are appropriate.

Subsequently, a battery 16 is attached to electronics 12, and enclosure 14 is hermetically sealed. Battery 16 is stored in the glovebox. Following baking, battery 16 is attached to the electronics package using, in this embodiment, a resistance weld 18. This is a conventional process, which can be readily carried out by those of ordinary skill in the art.

Alternatively the battery connections could be made as described in U.S. Pat. No. 5,103,818. Such an embodiment utilizes a plug and socket arrangement which is subsequently fusion welded. Following the electrical connection of the electronics package and battery 16 are hermetically sealed. Any other suitable connection arrangement could be used, being in mind the need to operate in the controlled environment.

It is known that battery 16 itself can be suitably sealed so as to not provide a source of moisture within the package, and this can be controlled separately during the battery manufacture. One method of controlling battery moisture content is described in JP08343907, which is hereby incorporated by reference herein. This reference discloses manufacturing in a low moisture environment, and the use of a moisture absorbent powder. As such, battery 16 may then be sealed, separately from electronics 12.

Figure 2:
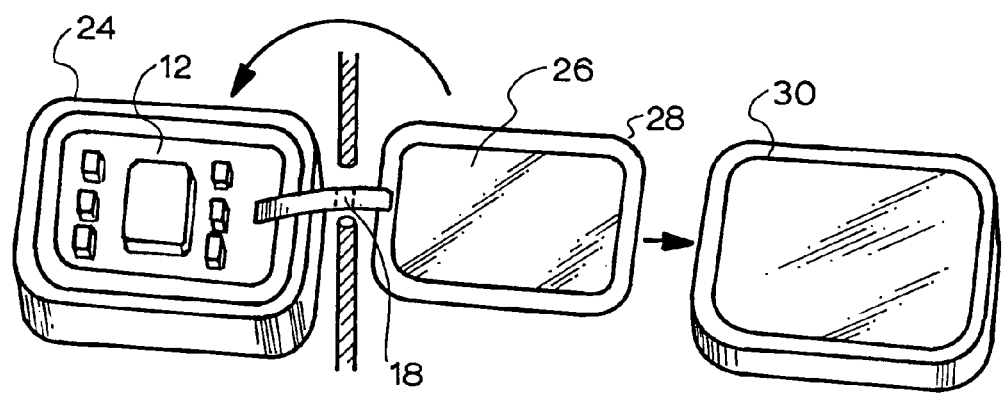
FIG. 2 is a perspective view illustrating another implementation of the present invention.

In the embodiment illustrated in FIG. 2, battery 26 is shaped with a flange 28 so as to form the lid of electronics enclosure 24. The outer surface of the battery structure will need to be formed from a suitable biocompatible material, for example titanium. Laser welding 30 around the edge of battery 26 then creates a hermetically-sealed enclosure. Such welding is a conventional process in the manufacture of implantable devices.

Battery 26 may be connected by welds 18 to positive and negative terminals in device electronics 12. However, it is preferred that the case of battery 26 provides one contact to battery 26, and laser weld 30 then creates one electrical connection via implant enclosure 24, so that only one resistance weld 18 is required, as shown in FIG. 2. Embodiments of this method of battery connection using enclosure 24 as a terminal is described in U.S. Pat. No. 5,814,091, which is incorporated by reference herein. Embodiments of the present invention may be conveniently used with a chassis design, such as disclosed in International Patent Application PCT/US2006/02794, which is hereby incorporated by reference herein. It is noted that as the device forms a complete metal enclosure with the other battery terminal inside the enclosure, there is no risk of a charge being delivered externally.

Embodiments of the present invention may be deployed for any shape of device, and for devices made from any suitable material. Whilst the examples describe a metal enclosure, the invention may equally be employed with ceramic or other materials, with suitable modification to sealing techniques. Obviously, in such an arrangement the ceramic housing could not be used as a conductor.

Battery energy is a function of the volume of the battery. By making the battery area most of, or the whole of, the area of the electrical enclosure the thickness of the battery can be minimized while obtaining an adequate volume.

The constructions shown in FIGS. 1 and 2 show a relatively shallow, wide construction with the seal applied to a large surface area. As such, a battery thickness of less than approximately 2 mm can be achieved.

For example, the power required to power a typical cochlear implant is about 5 mW. Using current battery technology, energy density is typically about 0.15 mWh/mm$^3$. Hence, to deliver about 5 mW with a 24 hour life requires a battery volume of about 800 mm$^3$. Hence, according to this implementation of the present invention, with an implant electrical package measuring about 25 mm square, the thickness of the battery can be about 1.3 mm. Techniques may be used to minimize battery dimensions such as that described in U.S. Pat. No. 6,040,082. This in turn minimizes the thickness of the implant.

In combination with PCT/US2006/02794, by the present applicant previously incorporated by reference herein, an overall implant thickness of less than 6 mm can be achieved. The positioning of the battery over the electronics also serves to provide additional protection to the electronics from impact.

It will be appreciated that the present invention can be implemented in a variety of ways, in combination with existing and new construction techniques, and variations and additions are possible using the underlying principles of the present invention.

All documents, patents, journal articles and other materials cited in the present application are hereby incorporated by reference.

The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

The invention claimed is:

1. A method of forming an implantable device, comprising:
    baking an open body containing electronic components so as to reduce the moisture content;
    connecting a heat sensitive component to said open body, wherein the heat sensitive component is integral with a sealing flange;
    sealing the open body to form said device; and
    wherein an open surface of the open body has a relatively large surface area, and the heat sensitive component is a battery.

2. The method of claim 1, further comprising positioning the battery within the open body and aligning the sealing flange of the battery with a perimeter of the open body.

3. The method of claim 1, wherein the step of baking the open body comprises baking the open body at approximately 125 degrees Celsius under vacuum.

4. The method of claim 1, wherein the step of baking the open body comprises baking the open body for approximately 16 hours.

5. The method of claim 1, further comprising laser welding around an edge of the battery to create a hermetically sealed enclosure.

6. A method of forming a sealed device, the device including electronic components and at least one heat sensitive component, the method comprising:
    baking an open body containing electronic components so as to reduce the moisture content;
    connecting a heat sensitive component to said open body, wherein the heat sensitive component is a battery;
    positioning the battery within the open body such that the battery substantially covers the open body; and
    sealing the open body to form said device.

7. The method of claim 6, wherein the step of positioning the battery within the open body comprises aligning a sealing flange of the battery with a perimeter of the open body.

8. The method of claim 6, wherein the open body has an open surface with a relatively large surface area.

9. The method of claim 6, wherein the step of baking the open body comprises baking the open body at approximately 125 degrees Celsius under vacuum.

10. The method of claim 6, wherein the step of baking the open body comprises baking the open body for approximately 16 hours.

11. The method of claim 6, further comprising laser welding around an edge of the battery to create a hermetically sealed enclosure.

* * * * *